(12) United States Patent
Ahola et al.

(10) Patent No.: US 6,764,690 B2
(45) Date of Patent: Jul. 20, 2004

(54) DISSOLVABLE OXIDES FOR BIOLOGICAL APPLICATIONS

(75) Inventors: Manja Ahola, Turku (FI); Heidi Fagerholm, Parainen (FI); Ilkka Kangasniemi, Turku (FI); Juha Kiesvaara, Littoinen (FI); Pirjo Kortesuo, Turku (FI); Kauko Kurkela, Espoo (FI); Niilo Saarinen, Turku (FI); Antti Yli-Urpo, Littoinen (FI)

(73) Assignee: DelSiTech Oy, Turku (FI)

( * ) Notice: Subject to any disclaimer, the term of this patent is extended or adjusted under 35 U.S.C. 154(b) by 0 days.

(21) Appl. No.: 10/178,718

(22) Filed: Jun. 25, 2002

(65) Prior Publication Data

US 2003/0021820 A1 Jan. 30, 2003

Related U.S. Application Data

(63) Continuation of application No. 09/194,256, filed as application No. PCT/FI97/00330 on May 29, 1997, now abandoned.
(60) Provisional application No. 60/018,575, filed on May 29, 1996, and provisional application No. 60/042,423, filed on Mar. 27, 1997.

(51) Int. Cl.$^7$ ............................ A61F 13/00; A61F 2/00; A61K 9/14
(52) U.S. Cl. ...................... 424/422; 424/423; 424/424; 424/425; 424/426; 424/484; 424/485
(58) Field of Search ................................ 424/422, 423, 424/424, 425, 426, 484, 485

(56) References Cited

U.S. PATENT DOCUMENTS

| | | | |
|---|---|---|---|
| 3,538,230 A | | 11/1970 | Pader et al. |
| 3,907,954 A | * | 9/1975 | Mansmann et al. ........... 264/63 |
| 4,180,566 A | | 12/1979 | Winyall et al. |
| 4,279,879 A | | 7/1981 | Winyall et al. |
| 4,353,890 A | | 10/1982 | Scott |
| 4,767,433 A | * | 8/1988 | Iura et al. ..................... 65/21.1 |
| 4,798,786 A | | 1/1989 | Tice et al. |
| 5,278,284 A | * | 1/1994 | Lusk et al. .................. 530/305 |
| 5,292,515 A | | 3/1994 | Moro et al. |
| 5,409,683 A | * | 4/1995 | Tillotson et al. ............ 423/338 |
| 5,505,966 A | | 4/1996 | Edman et al. |
| 5,510,109 A | | 4/1996 | Tomioka et al. |
| 5,605,700 A | | 2/1997 | DeGregorio et al. |
| 5,612,049 A | * | 3/1997 | Li et al. ...................... 424/422 |
| 5,709,873 A | | 1/1998 | Bar-Shalom et al. |
| 5,886,049 A | | 3/1999 | Itoh et al. |
| 5,911,658 A | * | 6/1999 | Yoldas ........................ 516/101 |
| 5,912,257 A | | 6/1999 | Prasad et al. |
| 6,156,223 A | * | 12/2000 | Sigel et al. .................... 252/62 |
| 6,353,038 B1 | * | 3/2002 | Aho et al. .................. 523/105 |
| 6,387,386 B1 | | 5/2002 | Levy |
| 6,395,299 B1 | * | 5/2002 | Babich et al. .............. 424/484 |

FOREIGN PATENT DOCUMENTS

| | | |
|---|---|---|
| EP | 336 014 | 10/1989 |
| EP | 680 753 | 11/1995 |
| WO | WO 96/03117 | 2/1996 |
| WO | WO 96/03117 A1 * | 2/1996 |

OTHER PUBLICATIONS

Unger et al., "The Use of Porous and Surface Modified Silicas as Drug Delivery and Stabilizing Agents," Drug. Development and Industrial Pharmacy 9(1&2), 69–91 (1983).

(List continued on next page.)

*Primary Examiner*—Thurman K. Page
*Assistant Examiner*—S. Tran
(74) *Attorney, Agent, or Firm*—James C. Lydon

(57) ABSTRACT

Controllably dissolvable silica-xerogels prepared via sol-gel process and their use. A delivery device including controllably dissolvable silica-xerogel into which structure a biologically active agent is incorporated. Pharmaceutical preparations including this device. Medical devices for orthopedic and surgical purposes which contain controllably dissolvable silica-xerogels, which may further include a biologically active agent.

12 Claims, 1 Drawing Sheet

PERCENTAGE OF THE REMAINING SILICA-XEROGEL IMPLANT AND $^3$H-TOREMIFENE ACTIVITY AT DIFFERENT TIME POINTS IN VIVO.

OTHER PUBLICATIONS

Sato et al., "Control of Pore Size Distribution of Silica Gel Through Sol–Gel Process Using Water Soluble Polymers as Additives," Journal of Materials Science 25, 4880–4885 (1990).

Avnir et al., "Enzymes and Other Proteins Entrapped in Sol–Gel Materials," Chem. Mater. 6, 1605–1614 (1994).

Ahola et al., "The Evaluation of Biocompatibility and Degradation of Non–Sintered Silica Xerogel Carrier Materials In Vivo," Transactions of the Society for Biomaterials, $23^{rd}$ Annual Meeting of the Society for Biomaterials, vol. XX, New Orleans, USA, p. 364, Apr. 30–May 4 (1997).

* cited by examiner

DISSOLVABLE OXIDES FOR BIOLOGICAL APPLICATIONS

This application is a continuation of application Ser. No. 09/194,256, filed Feb. 4, 1999, the contents of which are incorporated by reference herein, and which is the U.S. National Phase application of International application PCT FI97/00330, filed May 29, 1997 now abn, which claims benefit of 60/018,575 May 29, 1996 and 60/002,423 Mar. 27, 1999.

TECHNICAL FIELD OF THE INVENTION

The present invention is directed to controllably dissolvable sol-gel produced silica-xerogel materials and their use. Specifically, the present invention is directed to controllably dissolvable silica-xerogel particles of small diameter, prepared via sol-gel process where the gelation of the sol and evaporation of the solvent occur simultaneously. More specifically, the invention is directed to controllably dissolvable silica-xerogel particles of small diameter, prepared via sol-gel process where the gelation of the sol and evaporation of the solvent occur by a spray drying method or by a fiber spinning or drawing technique. Further, the invention is directed to controllably dissolvable sol-gel produced silica-xerogels as sustained and/or controlled release delivery devices for biologically active agents, especially medicines, proteins, or hormones, and to pharmaceutical preparations comprising said devices. Further, the invention is directed to implantable and transmucosal forms of said devices. And further, the invention is directed to implantable medical devices comprising controllably dissolvable sol-gel produced silica-xerogels, which may further comprise a biologically active agent.

BACKGROUND OF THE INVENTION

Silica-xerogels are partially hydrolyzed oxides of silicium. Hydrolyzed oxide gels can be produced by a sol-gel process, which has been used for producing ceramic and glass materials for many years.

The sol-gel process is based on hydrolyzation of a metal-alkoxide and subsequent polymerization of the metal hydroxides as follows:

1) $Si(OR)_4 + H_2O \rightarrow HO\text{-}Si(OR)_3 + ROH$
2) $HO\text{-}Si(OR)_3 + 3H_2O + ROH \rightarrow Si(OH)_4 + 4ROH$
3) $Si(OH)_4 + Si(OH)_4 \rightarrow (HO)_3Si\text{—}O\text{—}Si(OH)_3 + H_2O$ When the polymerization reaction goes further, additional chains, rings, and three dimensional networks are formed, and a gel comprising water, the alcohol of the alkoxy group and the gel itself is formed. The sol may also contain other additives such as acids or bases used for catalysis of the reaction. If alcohol and water are now extracted from the gel by washing and evaporating, a xerogel is obtained.

During drying large shrinking occurs creating internal stresses into the gel. If the monolithic gel is not allowed sufficiently time to relax its internal stresses, it will crack. During drying further polymerization of the remaining OH-groups occurs. The continuing polymerization carries on for a long time after gelation. This is called aging. The further the polymerization goes on, the more stable the gel or xerogel becomes. However, at room temperature the polymerization will effectively stop after a few weeks aging and the xerogel will not become totally inert. If the temperature is raised, the polymerization reaction can be accelerated, further stabilization and shrinkage occurs, and more internal stresses are introduced into the xerogel.

If the temperature is raised high enough (around 1000° C. for monolithic Si-gels) the gel or xerogel becomes a pure oxide and there are no OH-groups present in the material. However, in case of pure oxides, the reaction rate is extremely slow. If the oxides are incorporated with other ions, such as Na, K, Mg, or Ca, the reaction rate can be greatly increased. The so called bioactive glasses are developed from these systems. The dissolution rate of these glasses is controlled by the composition and surface area of the glass. These glasses are melted above 1000° C.

The general principles of mixing organic substances with gels are well known. The basic idea is that an organic substance is added to the sol-stage of the sol-gel process. Then, after gelation, the organic part has become an inherent part of the material. In conventional glass melting processes, this is not possible at all because the temperatures are much too high for organic substances to survive.

The sintering temperature is naturally a limiting factor also for many substances in organically modified silicates (ORMOSILS). In the case of medicines, the sintering temperature is limited by the breakdown of the structure or functionality of the medicine. For proteins, enzymes, antibodies and whole cells, the sintering limit is as low as 40° C. since they will begin coagulating at and above that temperature.

Organic substances are generally added to silica gels to modify the natural properties of the silicates with those of the organic substances. Some combinations of dopants and matrices used thus far are disclosed in Chemistry of Materials (1994) 6:1605–1614 (D. Avnir et al.).

Silicium sol-gel material directed for oral short term (less than 24 hours) drug delivery and methods of mixing drugs with silica-viscous sol have been described in Drug Development and Industrial Pharmacy (1983) 9 (1&2):69–91 (K. Unger et.al). The article describes a polycondensation in solution method, which starts with mixing polyethoxysiloxane (PES) with a solution of the drug in an appropriate solvent, giving a molecular scale entrapment of the drug in the polymer. The release rate of the drug is controlled by diffusion through the pores of the matrix material.

Published application EP 0680753 describes a sol-gel produced silica coating and particles containing a biologically active substance where the release rate of the active agent is controlled by addition of penetration agents, such as polyethylene glycol or sorbitol.

Published application WO 96/03117 discusses bone bioactive controlled release carriers comprising silica-based glass providing for the controlled release of biologically active molecules, their methods of preparation and methods of use. These carriers are stated to be prepared using a sol-gel-derived process.

SUMMARY OF THE INVENTION

An object of the present invention is to provide controllably dissolvable silica-xerogels prepared via a sol-gel process. A further object of the invention is to provide controllably dissolvable silica-xerogel particles of small diameter prepared via sol-gel process, where the gelation of the sol and evaporation of the solvent occur simultaneously. Specifically, the present invention provides controllably dissolvable silica-xerogel particles of small diameter prepared via sol-get process, where the gelation of the sol and evaporation of the solvent occur by a spray drying method or by a fiber spinning or drawing technique.

A further object of the invention is to provide sustained and/or controlled release delivery devices for biologically active agents, especially medicines, proteins, or hormones, which are made of controllably dissolvable sol-gel produced silica-xerogel, and pharmaceutical preparations comprising said devices. Specifically, the present invention provides sustained and/or controlled release delivery devices for biologically active agents, which are made of controllably dissolvable silica-xerogel particles of small diameter prepared via sol-gel process, where the gelation of the sol and evaporation of the solvent occur simultaneously, and pharmaceutical preparations comprising said devices.

A further object of the present invention is to provide a method of administering a biologically active agent to a human or animal body, which comprises implanting, injecting, or transmucosally attaching to a human or animal body a delivery device made of a sol-gel produced, controllably dissolvable silica-xerogel according to the present invention, in which structure a biologically active agent is incorporated.

A further object of the present invention is to provide an implantable medical device comprising controllably dissolvable sol-gel-produced silica-xerogel, which may further comprise a biologically active agent.

DISCRIPTION OF THE INVENTION

Figure 1:
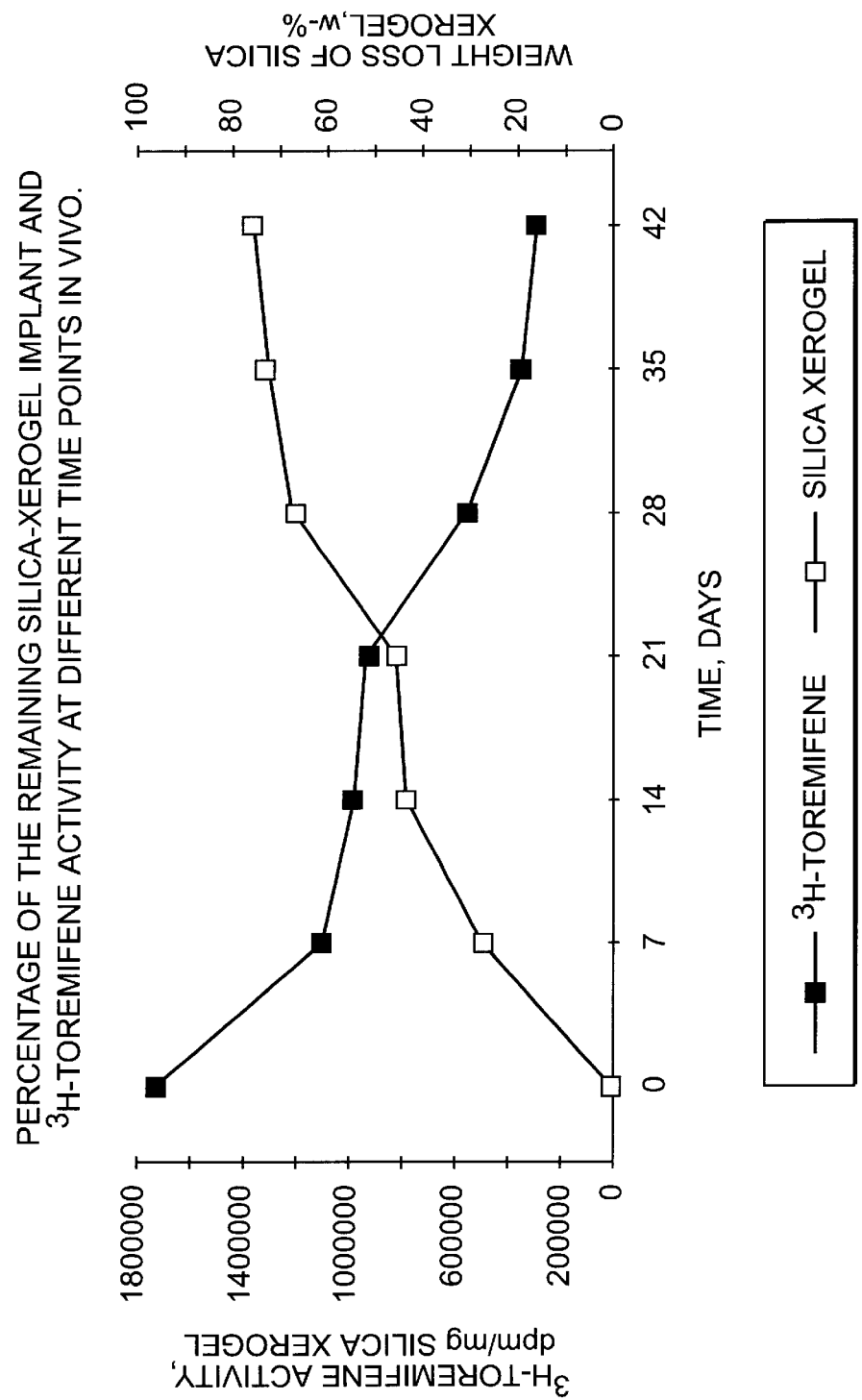
FIG. 1 shows graphically the percentage of the remaining silica-xerogel implant and $^3$H-toremifene activity at different time points of the in vivo experiment of Example 5.

Applicants have discovered that silica-xerogels prepared via a sol-gel process, and silica-xerogel particles of small diameter prepared via sol-gel process where the gelation of the sol and evaporation of the solvent occur simultaneously, dissolve controllably for a long (more that 24 hours) period of time. Further, the biologically active agents incorporated into the silica-xerogel structure are also released controllably for a long period of time. Therefore, the silica-xerogels of the invention can be used for a long-term delivery of biologically active agents. Thus, they can be used for delivery devices or pharmaceutical preparations that are, for example, implanted or injected into, or transmucosally attached to a human or animal body. Administration into any tissue, soft tissues or bone, is possible. This allows local application so that targeting of the biologically active agent release site is possible. Therefore, the maximum effect from the agent is received.

A delivery device or a pharmaceutical preparation is implantable subcutaneously; intramuscularly; intraosseously; in oral, sinuidal, and uteral cavities; and into any diseased tissue. Transmucosally attached delivery devices or pharmaceutical preparations can be, e.g., particles, such as spheres, administered as a spray into sinuidal or lung tissue where they will dissolve and release the biologically active agent. Similarly, small particles can be injected in a carrier fluid in the tissues.

It has also been found that the silica-xerogels of the invention can be used for implantable medical devices. A medical device of the invention can be implanted into any human or animal tissue. Silica-xerogels of the invention dissolve totally during the period desired when they are in contact with body fluids. Thus, delivery devices and medical devices of the invention dissolve totally and controllably.

In this connection, a delivery device is a silica-xerogel incorporated with a biologically active agent into the structure. A pharmaceutical preparation, such as a granulate or capsule, in this context is a preparation that comprises the delivery device and possibly additional excipients useful in pharmaceutical preparations. A medical device of the invention is also useful for orthopedic and surgical purposes and need not contain a biologically active agent incorporated into the structure of the silica-xerogel. A medical device may be, e.g., a woven or nonwoven mat made of silica-xerogel fibers.

The silica-xerogel material of the invention has been found to be very biocompatible. In other words, it does not adversely affect the surrounding tissue, e.g., by causing an inflammation reaction.

The silica-xerogel of the invention dissolves controllably, and the release of the biologically active agent from the silica-xerogel of the invention is based on this dissolution, which allows constant local release of the biologically active agent into the tissue. The release rate of the biologically active agent can be controlled via processing parameters of the gelation conditions such as spray drying temperature. Also factors such as the surface area/volume ratio of the material, the elemental composition of the silica-xerogel, and the dimension of the gel, which allows faultless silica-xerogels to be produced, control the release rate of the biologically active agent.

The silica xerogel matrix and the incorporated biologically active agent are released slowly when diameter of the xerogel particles is in the order of about 1–500 µm. When the diameter of the particles is increased, the release rates of the matrix and the active agent are also increased.

The biologically active agent can be any organic or inorganic agent that is biologically active. The biologically active agent can be, e.g., a medicine, a protein, a hormone, a living or dead cell, a bacteria, a virus or a part thereof. Biologically active agents include those especially useful for long-term therapy, such as hormonal treatment, e.g., contraception and hormone replacement therapy and for the treatment of osteoporosis, cancer, epilepsy, Parkinson's disease, pain, and cognitive dysfunction. The suitable biologically active agents may be, e.g., anti-inflammatory agents, anti-infectives (e.g., antibiotics and antiviral agents, such as glindamycin, miconazole), analgesics and analgesic combinations, antiasthmatic agents, anticonvulsants (e.g., oxycarbazepine), antidepressants, antidiabetic agents, antineoplastics, anticancer agents (e.g., toremifene, tamoxifene, taxol), antipsychotics, antispasmodics, anticholinergics, sympatomimetics, cardiovascular preparations, antiarrythmics, antihypertensives, diuretics, vasodilators, CNS (central nervous system) drugs such as antiparkinsonism dugs (e.g., selegiline), steroidal hormones (e.g., estradiol, progesterone, nestorone), sedatives (e.g. atipamezole, dexmedetomidine, levomedetomidine), tranquilizers, and cognitive dysfunction drugs. The medicine can be in the form of a salt, such as selegiline hydrochloride, (-)-4-(5-fluoro-2,3-dihydro-1H-inden-2-yl)-1H-imidazole hydrochloride, 4-(5-fluoro-2,3-dihydro-1H-inden-2-yl)-1H-imidazole hydrochloride, dexmedetomidine hydrochloride and toremifene citrate. The medicine can also be in the form of a free acid, such as ibuprofen; a free base, such as coffein or miconatzole; or a neutral compound, such as Z-2-(4-(4-chloro-1,2-diphenyl-but-1-enyl)phenoxy) ethanol. A peptide can be e.g. levodopa, and a protein can be e.g., an enamel matrix derivative or a bone morphogenetic protein. An effective amount of a biologically active agent can be added to the reaction mixture at any stage of the process. However, it is preferable to add the biologically active agent to the reaction mixture at the sol-stage before polycondensation reaction takes place or mix it with the starting materials. The precise amount employed in a particular situation is dependent upon numerous factors, such as the method of administration, type of mammal, the condition for which the biologically active agent is administered, the particular biologically active agent used, the desired duration of use, etc. The amount of toremifene citrate in the silica-xerogel may vary from about 1 w-% to about 40 w-%.

The controllably dissolvable silica-xerogels of the invention can be prepared by allowing silica-alkoxide, such as tetraethylorthosilicate (TEOS), to react with water and optionally a solvent, e.g. ethanol or polyethylene glycol, or a combination of solvents, at low temperature, such as −20° C. to 100° C., preferably at room temperature, in the presence of an acidic, e.g. acetic acid, or a basic catalyst by hydrolyzation (sol is formed) and polycondensation (gel is formed). The catalyst should be chosen not harming the biologically active agent.

In contrast to the production of monolithic silica-xerogels and silica coatings, in producing silica-xerogel particles of small diameter, for example by a spray drying method or a fiber spinning or drawing method, the gelation of the sol and evaporation of the solvent occur simultaneously, forming controllably dissolvable particles of small diameter, such as spheres or fibers. When the gelation is allowed to be completed before evaporation of the solvent, the formed gel is a monolith extending from wall to wall of the container. In contrast, in the present invention where the gelation of the sol and evaporation of the solvent occur simultaneously, for example by a spray drying method or a fiber spinning or drawing method, the evaporation of the solvent from the sol forces the colloidal nano-sized gel particles already formed close to each other and forces them to react with each other thereby leading to the formation of silica-xerogel particles.

In the present invention, it has been shown that when the gel is produced in particles of small diameter, such as spheres and fibers, internal stresses of the gel formed during drying are avoided almost completely and the particles are slowly degradable.

Thus, slow release materials may now be produced at low temperatures without necessarily having to sinter at all, allowing for use of all organic substances as ingredients.

Dried and/or partially sintered gels, i.e., xerogels, comprise $SiO_2$ modified with OH-groups that break the continuous silica network. In order for these oxides to dissolve, hydrolyzation of the bonding between an oxygen atom and a metal atom must be broken, and a hydrogen atom takes the place of the metal. Thus, the metal oxide network becomes discontinuous. The hydrolyzation can advance all the way, breaking all metal to metal oxygen bonds untill the oxide has totally dissolved. The dissolution behaviour of xerogels depends on several parameters. The sintering or drying temperature is a parameter, which has an influence on the dissolution rate of the material. An increased sintering temperature increases the polycondensation reaction rate and final state. Other parameters that control the polycondensation reaction, such as $TEOS:H_2O$ molar ratio, pH of the silica sol, aging, gelation rate, shape, i.e., thickness of the gel, and, drying, have a minor influence on dissolution behaviour of gels sintered at low temperature (below 300° C). Further, different additives, such as polyethylene glycol or sorbitol which are used as penetration agents, have also only a minor effect on the release rate of the bioactive agent. The composition of the gel also has an influence on the dissolution behaviour, especially on materials sintered at above 200° C. The composition of the xerogel can be altered with elements such as Na, Ca, P, K, Mg, Cl, Al, B, Ti, N, Fe, and C.

Porosity and surface area of the silica-xerogel can be influenced by the sintering temperature and additives. When sintered at the same temperature, different additive compositions have a large influence to the porosity and surface area. However, this change has only a minor influence to the dissolution rate of the xerogels produced near room temperature. The dissolution rates of xerogels produced at high temperatures (500–1100° C.) will be influenced stronly by these factors.

Instead, the diameter of the single gel-object and the production method seem to have a profound influence on the dissolution rate of the xerogel. Particles of silica gel may be produced in different ways. The traditional crushing results in particles that dissolve at the same rate as the bulk material per unit surface area. In WO 9603117, the release of vancomycin from crushed silica xerogel particles of 500–700 $\mu$m is decribed. The release was very rapid and most of incorporated vancomycin (about 90%) released during the first day. In contrast, if for example the sol is spray dried into particles (below 200 $\mu$m) at room temperature and kept in an exciccator for 2 months, dissolution of incorporated drug will be constant and total dissolution will last for 6 days. The dissolution rate of the spray dried particles seems to be over six times slower than the dissolution rate of the crushed particles in vitro.

In the present invention, silica gel particles and spheres are produced by spray drying above the melting point of the silica sol. During spraying into air, the small droplets dry in the atmosphere sufficiently to result in gelation of the hydrolized silica ions and colloidal gel particles. If the droplets hit a surface before sufficient drying, they will form pseudo-spheres caused by surface energy differences between the droplet and the substrate. In that case, they will also gelate as pseudospheres. The gelated particles are heat treated or aged at room temperature which results in further polymerisation of the OH-groups. The heat or aging treatment slows the dissolution of the particles significantly. The particles can be incorporated with ions, such as Na, K, P, Ca, Mg, Al, and B, in order to produce dissolvable and/or bioactive bone bonding particles.

Spray drying of the gel particles without biologically active agent at the room temperature and aging them in an exciccator gives homogeneous, faultless particles with slow dissolution. These particles dissolve linearly at a rate of 1.9 w-% per week. From the at the room temperature spray dried particles with biologically active agent, silica released linearly at the rate of 22.4 w-% per week. Microspheres (<50 $\mu$m) containing 10 w-% biologically active agent, prepared by mini spray dryer (Buchi, Switzerland) at 132° C., dissolved at a rate of 77.3 w-% per week. Without a biologically active agent the release rate of 5.8 w-% per week was measured.

Controllably dissolvable silica-xerogel fibers can be produced by sol-spinning technique with further aging or treating with low temperature heat. The production temperature can be kept near room temperature. The fiber production techniques give homogeneous and faultless materials. Silica-xerogel fibers produced by a glass rod spinneret technique and kept in an exciccator for four months produced materials that dissolved 2.5 w-% per week. The fibres can be incorporated with ions, such as Na, K, P, Ca, Mg, Al, and B, in order to produce dissolvable and/or bioactive bone bonding fibers.

Vowen or nonvowen mats prepared from silica-xerogel fibers of the invention can be used to separate two or more types of tissues from each other. They can also be used as bone repair mats. It is advantageous if the tissue guide is dissolvable so that it does not need to be removed by second operation. The non-sintered and aged fibers of the invention were found to exhibit dissolution rates acceptable for such applications (10 w-% in 4 weeks).

A bone collecting filter is a medical device placed on a suction tube, which removes the debris and excess liquids from the operation site. When the surgeon is drilling, sawing, grinding or otherwise working on bony tissue the bone chips can be collected with the filter and placed back into the defect. So far, these filters are not dissolvable in the tissue. If these filters were made of sol-gel produced fibers or particles, they could be made dissolvable and loaded with a biologically active agent. Thus, the entire filter could be placed into the defect site with the bone chips.

The implants made of silica-xerogel fibermats are flexible and dissolvable.

Polylactic acid, polyglycolic acid and polykaprolacton are degradable polymers used in medical devices which, however, need to be reinforced to achieve and maintain sufficient strength long enough while the degradation reduces the strength of the matrix. Controllably dissolvable silica xerogel fibers and particles of the invention are ideal for this purpose since they have the sufficient strength and a controllable dissolution rate. They may also be used for strengthening plastic packing materials which may be made of polyiactic acid, starch or any other biodegradable polymer.

Sol-gel produced controllably dissolvable silica-xerogels according to the invention can be used as cell growth substrates in the form of for example, membranes and coatings made from spray dried particles or fibers. Cell growth assisting substances are released from the substrate with the dissolving silica.

The following examples are intended to illustrate the invention, and are not to be construed as being limitations thereon.

EXAMPLE 1

Production of Silica-Xerogel Monolith

A sol for the monolithic siliga gel was prepared from TEOS, distilled water and $CH_3COOH$ in 1/14.2/0.5 ratio. Polyethylene glycol was used as an additive in a 0, 0.005 (average molecular weight of 10,000), or 0.012 (average molecular weight of 4,600) ratio.

Silica-xerogels were prepared by the hydrolysis and polycondensation of TEOS with or without polyethylene glycol and water at room temperature. A small amount of a catalyst (acetic acid) was added to accelerate the reaction. Drug crystals were added to clear hydrolyzed solution, and silica sol was casted into wells of microtiter plate kept at 40° C. in an oven for hydrolysis, polycondensation and aging for 18 hours. The aged silica gels were soaked in water for two days to leach out residual organic within the gel and dehydrated at 40° C. to constant weight for a few days to obtain a silica-xerogel containing incorporated drug. A fraction of the silica xerogels were sintered at 80° C. or 120° C. (2° C./h, 2h at 80° C./120° C.). Toremifene citrate was used as model drug in studies, which evaluated the effect of PEG, sintering temperature and drug content on the release rate of drug and silica from the matrix.

In Vitro Dissolution Test

The dissolution profiles of toremifene citrate and silica from silica-xerogel were studied using the USP XXII dissolution apparatus II (paddle method, Sotax AT6, Basel, Switzerland) at constant temperature (37° C.). Simulated body fluid (SBF, pH 7.4) containing 0.5% (m/v) sodium dodecyl sulphate was used as dissolution medium. SBF was prepared by dissolving reagent grade NaCl (136.8 mM), $NaHCO_3$ (4.2 mM), KCl (3.0 mM), $K_2HPO_4 \times 3H_2O$ (1.0 mM), $MgCl_2 \times 6H_2O$ (1.5 mM), $CaCl_2 \times 2H_2O$ (2.5 mM) and $Na_2SO_4$ (0.5 mM) in distilled water. They were buffered at pH 7.4 with tris-(hydroxymethyl)aminomethane (50 mM) and hydrochloric acid.

The volume of dissolution medium was 250 ml. Agitation intensity was 50 rpm and temperature was 37° C.

The absorbance values of the dissolution samples were measured on an UV-visible spectrophotometer (Hewlett Packard 845/A, USA) at maximum absorbance of toremifene citrate ($A_{278}$). Dissolved silica was measured spectrophotometrically as a silica-molybdenblue complex at $A_{820}$ (Koch and Koch-Dedic, 1974).

Porosity

The porosity of the silica xerogel samples was measured using the high pressure porosimeter (autoscan 33, Quantachrome Corp. U.S.A.). Pore diameters of 6.5 nm–14 μm were measured.

Results

Toremifene citrate was added as crystal particles into reaction mixture, and it appeared as a molecular dispersion in silica gel matrix. The concentration of added toremifene citrate in silica sol varied between 1.9–5.5 wt-% (corresponding to about 11.5–34.4 wt-% of drug in the air dried gel). Higher amounts of toremifene citrate precipitated during gelation at 40° C.

The effect of the drug content was studied on sintered silica gels (120° C.) containing 11.5, 22.9 and 34.4 wt-% of toremifene citrate. The release profile of toremifene citrate was linear according to zero-order release kinetics. The release of toremifene citrate was slowest from silica-xerogel containing 11.5 wt-% drug (0.05%/mg implant/h) and fastest from silica xerogel with 34.4 wt-% drug (0.11%/mg implant/h). The silica matrix dissolved according to zero-order release.

The sintering of silica-xerogels at temperature ranges used did not show any significant effect on the release rate of toremifene citrate or silica.

Unger et al. indicate that water soluble polymers such as polyethylene oxides enhance the liberation of medicines from polycondensed silica gels. However, the release of toremifene citrate or silica from silica-xerogel cylinders was not enhanced by the added polyethylene glycol. Actually, toremifene citrate and silica release was fastest from silica-xerogels without polyethylene glycol. Toremifene citrate released linearly at the rate of 0.16%/mg implant/h and silica 0.31%/mg implant/h. From silica xerogels containing PEG 4600, toremifene citrate released linearly at the rate of 0.13%/mg implant/h and from xerogels containing PEG 10 000, 0.1%/mg implant/h. Also dissolution of silica was fastest from silica xerogel without PEG, 0.31%/mg implant/h. From xerogels containing PEG 4600, silica released linearly at the rate of 0.24%/mg implant/h and from xerogels with PEG 10 000 at the rate of 0.16%/mg implant/h.

A correlation between silica and toremifene citrate release was found, meaning that the release of toremifene citrate was mainly controlled by dissolution of the silica-xerogel matrix ($r_{mean}$=0.995).

Addition of PEG seems to decrease the total pore volume and surface area of pores especially in the 120° C. sintered samples. In earlier study water soluble polymers were used in the sol-gel process to control the pore size distribution (Sato et al., J. Mat. Sci. 25, 4880–85, 1990). In the study, PEG decreased the surface area and decreased the pore size.

TABLE 1

Porosity parameters of the silica xerogel samples (n = 2)

| SAMPLE | TOTAL PORE VOLUME (ml/g) | SURFACE AREA OF PORES (m²/g) | MEAN PORE SIZE (nm) | MEDIAN PORE SIZE (nm) |
|---|---|---|---|---|
| PEG 4,600 120° C. (n = 1) | 0.050 | 16.47 | 12.2 | 11.8 |
| no PEG 120° C. (n = 2) | 0.069 (0.001) | 22.01 (2.025) | 12.3 (0.5) | 12.0 (0.8) |
| PEG 10,000 120° C. (n = 2) | 0.042 (0.001) | 13.65 (0.43) | 12.4 (0.2) | 12.0 (0.5) |
| PEG 4,600 40° C. (n = 2) | 0.021 (0.001) | 5.84 (0.80) | 14.5 (1.1) | 15.6 (1.3) |
| no PEG 40° C. (n = 2) | 0.040 (0.007) | 12.51 (3.01) | 12.9 (1.1) | 12.3 (1.4) |
| PEG 10,000 40° C. (n = 2) | 0.038 (0.005) | 10.92 (0.75) | 13.9 (0.7) | 13.2 (0.9) |

Selegiline hydrochloride, (-)-4-(5-fluoro-2,3-dihydro-1H-inden-2-yl)-1H-imidazole hydrochloride, dexmedetomidine hydrochloride, ibuprofen, and coffein can also be incorporated into silica sol prepared above. Peptides (levodopa) and proteins (an enamel matrix derivative) can also be incorporated into the above silica sol.

EXAMPLE 2

Production of Silica Xerogel Fibers

A sol for the fiber drawing purpose was prepared from TEOS, distilled water, $HNO_3$, and ethanol in 1/2.0/0.036/1.0 ratio. The sol was allowed to form colloidal gel particles for 1 hour at 75° C. before drawing. Silica-xerogel fibers were prepared from the sol using a glass-rod spinneret technique. The fibers were drawn in the spinneret reactor, where the polycondensation occurred at 75° C. The viscosity of the sol at the start of fiber drawing was found to be approximately 10 mPas. The fibers were put into aqueous solution within 48 hours and 4 months later. The fibers were also treated at 300° C. and 700° C. (heating rate 10° C./h, 2 h at max.T) in addition to the fibers kept at room temperature. The fibers were dissolved into a tris-methylaminomethane-HCl-buffered water or simulated body fluid (pH=7.54, 23° C.; pH=7.40, 37° C.).

The silica, calcium and phosphate contents were analyzed from the solutions with atomic absorption spectroscopy; weigth loss of the fibers was measured; and SEM-EDX analysis was performed on the remaining fibers.

Results

The drawn fibers are smooth and, as-prepared, they are translucent. By light microscopy neither scattering nor cavities could be detected. The fibers were in amorphous state with respect to an x-ray diffraction pattern. Moreover, microcracking or flaw type failures could not be detected. The fiber surface drawn by glass-rod technique consists of small pores with diameters of about 100 nm. Only the fibers kept at room temperature (RT) dissolved at any significant amounts. The RT-fibers stored for 4 months in an excicator dissolved 10 w-% within 4 weeks.

The tensile strength of the as-prepared fibers was measured to be in the area up to 800 MPa for fibers of a diameter of about 10 μm. The Young's modulus of these fibres was measured to be in the area of 5 GPa. The strain-to-failure was above 10%, which is a typical value for glass fibers. The mechanical properties of the fibres are affected by the heat-treatment (drying) temperature.

Silica-Xeroael Fibers in Vivo

In this experiment, sintered (200° C., 400° C., 600° C., and 800° C.) and non-sintered silica-xerogel fibers were studied subcutaneously with rats. The fibers were sterilized with hot air, except the non-sintered fibers, which were sterilized in ethanol (70% for two hours, drying in an excicator for 2 days).

The animals were anesthesized with a solution of HYP-NORM (phentanyl citrate 0.315 mg/ml and fluanisone 10 mg/ml) and DORMICUM (midazolam maleate). The skin hair was removed. Two or three materials were implanted in the back subcutan of each animal. The animals were killed 2 weeks postoperatively. The tissue samples were embedded in PMMA, sectioned, ground and stained with toluidine blue or Von Kossa (5% silver nitrate solution, 0.1% safranine O solution and %5 sodium sulphate solution). The histological slices were analyzed light microscopically and scanning electron microspically.

Clinically, no swelling nor any signs of inflammation were observed. Wounds had healed well. In histological sections, no inflammatory reactions could be observed after two weeks postoperatively. Some slices contained macrophages in addition to fibroblasts, but the overall view appeared nonproblematic. In histological sections, toluidine blue stained the surroundings of the fibers blue, possibly because of the dissolved silica from the fibers. Almost all fibers had integrated well into the surrounding connective tissue. No signs of resorption of the fibers could be observed in SEM examination. No Ca, P-layer could be observed on the surface of the fibers. The inflammatory reaction caused by the fibers was negligible in rats.

EXAMPLE 3

Preparation of Silica-Xerogel Fibers Containing Toremifene Citrate

A sol for the fiber drawing purpose was prepared from TEOS, distilled water, $HNO_3$ and ethanol in 1/2.0/0.036/1.0 ratio. The sol was allowed to form colloidal gel particles at 75° C. and toremifene citrate (400 mg/ml) was dissolved in the sol after three hours. Before drawing the fibers by glass rod, the silica sol-gel was further allowed to form colloidal particles at 75° C. for 8.5 hours.

EXAMPLE 4

Production of Spherical Spray Dried Silica Xerogel Particles at Room Temperature TEOS, distilled water and acetic acid were mixed in 1:14.2:0.5 ratio at room temperature on a magnetic stirrer.

After hydrolyzation, the sol was sprayed into air and the droplets were allowed to fall freely onto a polymeric substrate and gelate completely before collecting. The gelated particles were kept in an exciccator for four days before the dissolution test.

5,5 mg of gel particles (0,5–1000 μm) were placed in 50 ml of simulated body fluid (SBF) at 37° C. and pH 7.4. The dissolution vessel was under gentle shaking movement during dissolution. Three parallel measurements were performed on each of the three parallel samples after 171, 336 and 504 hours. The particles dissolved 1.9 w-% within a week.

The spray dried particles (60–200 μm) containing toremifene citrate were prepared by the above method. Toremifene citrate at the concentration of 20 mg/ml was dissolved in silica sol for spray drying after 1 hour hydrolyzation.

Dissolution of the drug and silica from silica-xerogel particles containing 10.2 w-% toremifene citrate were studied as described in example 1 after two months from preparation. Toremifene citrate and silica released linearly from the particles. Toremifene citrate released at the rate of 0.68 w-% per hour and silica 0.13 w-% per hour.

EXAMPLE 5

Production of Silica-Xerogel Discs Containing Toremifene

A sol for the monolithic silica-xerogel was prepared from tetraethoxysilane (TEOS, Aldrich), deionized water, acetic acid ($CH_3COOH$, J. T. Baker), and polyethylene glycol (PEG, Mw 4600, J. T. Baker) in a 1/14.2/0.5/0.0012 ratio at room temperature (RT). Toremifene citrate (33 mg/g) and $^3$H-treated toremifene (16 μCi/g) were added to the solution. The solution was cast in blister-plate wells (100 μl/well) and kept at 40° C. for hydrolysis, polycondensation, and aging for 18 hours. The aged silica-xerogel was dried at 40° C. to constant weight.

Toremifene Loaded Silica-Xerogels Discs In Vivo

Sixty female mice (C57B1, Denmark) with the average weight of about 19.6 g (SD 1.2) were studied. The animals were divided into two experimental groups (5 mice in each group): a toremifene treated silica-xerogel group and untreated silica-xerogel group. The animals were treated for 7, 14, 21, 28, 35, and 42 days. The $^3$H-toremifene dose was about 80 μCi/kg (0.8 μCi/implant); toremifene citrate, 350 mg/kg (appr. 3.4 mg/implant); and silica gel, about 1.53 g/kg body weight. A toremifene loaded silica-xerogel disc was implanted subcutaneously an each side of the backbone.

After a predetermined period of time the silica-xerogel discs on the left side of the backbone were explanted together with the surrounding tissue, fixed in 70% ethanol, and embedde in Technovit (Algol). Sections of 20 μm were stained with toluidine blue. Samples of liver, kidney, and lymph node were fixed in buffered formaldehyde (Merck) and embedde in paraffin. Sections of 6 μm were stained with hematoxylin eosin. All tissue samples were evaluated using light microscopy. The silica-xerogel discs on the right side of the backbone were cut out from the surrounding fibrous capsule and dried at RT in a desicator for 24 hours. Their weights were determined and the precentage of implant remaining at each point was calculated.

To determine the amount of toremifene remaining in the implants, the dried discs were dissolved in 0.1 N NaOH and the activity was measured in a liquid scintillation counter (model 81000, LKB-Wallac, Turku, Finland). After sacrifice of the mice, the tissue samples taken from the application area were burned in an oxidizer (Junitek, Kaarina, Finland).

The weight loss of the silica-xerogel matrix was about 75 w-% during 42 days. The erosion rate was fast during 28 days and then decreased as seen from FIG. 1. The silica-xerogel discs showed sustained release of toremifene during the test period. The amount of $^3$H-toremifene remaining in the implant after 42 days was still about 16% (see FIG. 1). The release rate of toremifene was controlled by the bio-erosion of the silica-xerogel matrix. The correlation between silica and $^3$H-toremifene release was r=0.9890.

The untreated silica-xerogel implant did not cause irritation at the implantation site. A fibrotic capsule formed around the implant. No extensive silica-xerogel related systemic toxicity could be observed. The silica-xerogel gave sustained release for over six weeks. According to the above study, the silica-xerogels are biocompatible and controllably dissolvable. Thus, the silica-xerogel is a suitable carrier for a long term implantable delivery system.

EXAMPLE 6

Production of Spherical Spray Dried Silica-Xerogel Particles Containing Toremifene at pH 3.8 by Mini Spray Dryer A sol for spray drying purpose was prepared from TEOS, distilled water and acetic acid in 1:14.2:0.5 molar ratio at room temperature on a magnetic stirrer. After hydrolyzation toremifene citrate was dissolved (20 mg/ml) and the sol was spray dried by mini spray dryer (Buchi, Switzerland). The pH of the sol was 3.8 after addition of toremifene citrate. The spray drying conditions were following: inlet temperature 134° C., flow 600, aspirator 90, pump 16.

About 40-50 mg of gel particles (<50 μm) were placed in 250 ml of simulated body fluid (SBF) at 37° C. and pH 7.4. The dissolution profiles of toremifene citrate and silica were studied using the USP XXII dissolution apparatus II (paddle method, Sotax AT6, Basel, Switzerland).

The release profile of toremifene citrate was linear according to the square root of time kinetics. After 30 hours 80 w-% of toremifene citrate was released. The release of silica was linear. Silica microspheres dissolved at a rate of 0.46 w-% per hour.

EXAMPLE 7

Production of Spherical Spray Dried Silica-Xerogel Particles Containing Toremifene Citrate at pH 2 by Mini Spray Dryer: Effect of Aging The solution for spray drying purpose was prepared with a mole ratio of TEOS:$H_2$O:HCl=1.0:14.2:0.003. Toremifene citrate was dissolved after one hour hydrolyzation at the concentration of 20 mg/ml. The pH of the sol with toremifene citrate was about 3.8. Before spray drying the pH of the sol was adjusted to pH 2.1 with hydrochloric acid. Silica sol was spray dried immedeately or after 65 hours aging at room temperature. The spray drying conditions were as described in Example 6. Dissolution of toremifene citrate and silica was performed as in Example 6.

The release of toremifene citrate and silica was according to square root of time kinetics (table 2). After 30 hours 63.1 w-% of toremifene citrate was released from the aged silica microspheres and 75.2 w-% from the unaged. The release of toremifene citrate was about 20% slower from aged microspheres. The release of silica from aged microspheres is about 20% slower than from unaged.

TEOS ratios. Also degradation rate of the matrix containing PEG with $H_2O$/TEOS ratio 6 was faster (25–50%) than degradation of matrix with $H_2O$/TEOS ratio 14 (table 4).

TABLE 2

Release of toremifene citrate and silica from microspheres aged for 65 h and without aging containing 11 w % toremifene citrate.

| Toremifene citrate | aged for 65 h (pH 2) | aged for 0 h (pH 2) |
|---|---|---|
| slope (%/h$^{1/2}$) | 9.79 | 12.2 |
| correlation coefficient | 0.9713 | 0.9888 |
| cum released toremifene (%) after 30 h | 63.1 | 75.2 |
| Silica | | |
| slope (ug/h$^{1/2}$) | 928.22 | 1047.47 |
| correlation coefficient | 0.9826 | 0.9898 |

EXAMPLE 8

Release of Toremifene From Crushed Silica Xerogel Particles

A sol was prepared as described in Example 1 for monolithic silica-xerogel from TEOS, distilled water and acetic acid in a molar ratio 1:14.2:0.5. Polyethylene glycol (average molecular weight of 4.600) was used as an additive at a concentration 10 mg/ml. Toremifene citrate was dissolved in hydrolyzed sol at the concentration of 40 mg/ml. Silica sol was casted into test tubes kept at 40° C. in an oven for hydrolysis, polycondensation and aging for 18 h. Polymerized silica gel was crushed and dried to constant weight. Granules were in a size range of about 4–50 µm in diameter.

About 42 mg of gel particles were placed in 250 ml of simulated body fluid (SBF) at 37° C. and pH 7.4. The dissolution profiles of toremifene citrate and silica were studied using the USP XXII dissolution apparatus II (paddle method, Sotax AT6, Basel, Switzerland).

Toremifene citrate dissolved linearly according square root of time kinetics at rate of 8.1%/h$^{1/2}$. Silica xerogel matrix dissolved linearily at a rate of 0.2% per hour.

EXAMPLE 9

Production of Silica Xerogel Monolith Containing Toremifene Citrate: Effect of TEOS:$H_2O$ Ratio and Water Soluble Polymers on Dissolution of Toremifene Citrate and Silica Silica gels were prepared from TEOS, water, ethanol and HCl in the molar ratio 1:6:2.3:0.003 or 1:14:2.3:0.003 at room temperature. Polyethylene glycol (average molecular weight of 10,000 or 4,600) was used as additive at the concentration of 10 mg/ml and toremifene citrate at the concentration of 20 mg/ml. Hydrolyzed sol was casted into wells of blister plate, kept at 40° C. in an oven for hydrolysis, polycondensation and aging for 18 hours. The silica gels were dried at 25° C. in a desiccator at 11% relative humidity to constant weight to obtain a silica xerogel containing incorporated toremifene citrate.

Dissolution profiles of toremifene citrate and silica were studied as in Example 1.

Release of toremifene citrate and degradation of silica matrix was studied at two different $H_2O$:TEOS molar ratios (14:1 and 6:1). Release of toremifene citrate was faster from silica matrix containing PEG with $H_2O$:TEOS ratio 6 than from matrix containing PEG with $H_2O$:TEOS ratio 14 (table 3). Without PEG the release rate was equal for both $H_2O$/TEOS ratios. Also degradation rate of the matrix containing PEG with $H_2O$/TEOS ratio 6 was faster (25–50%) than degradation of matrix with $H_2O$/TEOS ratio 14 (table 4).

TABLE 3

Release of toremifene citrate from silica xerogels containing 1 w % PEG of different molecular weight.

| | PEG 4600 | PEG 10000 | without PEG |
|---|---|---|---|
| $H_2O$/TEOS = 14:1 | | | |
| SLOPE %/mg IMPLANT × h | 0.052 | 0.061 | 0.085 |
| CORRELATION COEFFICIENT | 0.9895 | 0.9902 | 0.9903 |
| $H_2O$/TEOS = 6:1 | | | |
| SLOPE | 0.094 %/mg × h | 0.922 %/mg IMPLANT × h$^{1/2}$ | 0.657 %/mg IMPLANT × h$^{1/2}$ |
| CORRELATION COEFFICIENT | 0.9773 | 0.9915 | 0.9909 |

TABLE 4

Release of silica from silica xerogels containing 1 w % PEG of different molecular weight.

| | PEG 4600 | PEG 10000 | WITHOUT PEG |
|---|---|---|---|
| $H_2O$/TEOS = 14:1 | | | |
| SLOPE %/mg IMPLANT × h | 0.097 | 0.168 | 0.176 |
| CORRELATION COEFFICIENT | 0.9933 | 0.9896 | 0.9902 |
| H2O/TEOS = 6:1 | | | |
| SLOPE %/mg IMPLANT × h | 0.188 | 0.221 | 0.181 |
| CORRELATION COEFFICIENT | 0.9896 | 0.9770 | 0.9743 |

EXAMPLE 10

Production of Silica Xerogel Monolith Containing Toremifene Citrate: Effect of Aging and Drying Conditions A sol was prepared as described in Example 1. Polyethylene glycol (Mw 4,600) was used as an additive (10 mg ml). Toremifene citrate was dissolved at the concentration of 20 mg/ml in the hydrolyzed sol after 1 hour. Sol was casted into wells of blister plate and kept at 40° C. for 18 hours. Thereafter the gels were transferred to air tight test tubes for aging at 40° C. for 7 or 28 days. Aged silica gels were dried to constant weight at 25° C. at different relative humidities (11.4%, 48.4% and 74.7%).

Dissolution of toremifene citrate and silica was studied as described in Example 1.

Silica dissolved linearly from all silica xerogel samples. Aging time did not affect the degradation rate of silica matrix (table 6). Toremifene citrate dissolved according to square root of time kinetics (table 5). Release of toremifene citrate was sligthly faster (about 30%) from 28 days aged silica xerogels than from unaged.

TABLE 5

Dissolution of toremifene citrate from aged silica xerogels

| AGING, DAYS | 11.4 RH % | 48.4 RH % | 74.7 RH % |
|---|---|---|---|
| 0 | r = 0.9808<br>b = 0.46%/mg implant/h$^{1/2}$ | r = 0.9924<br>b = 0.53 | r = 0.9728<br>b = 0.46 |
| 7 | r = 0.9869<br>b = 0.59 | r = 0.9866<br>b = 0.52 | r = 0.9943<br>b = 0.06%/mg implant/h |
| 28 | r = 0.9974<br>b = 0.67 | r = 0.9917<br>b = 0.74 | — |

TABLE 6

Dissolution of silica from aged silica xerogels

| aging, days | 11.4 RH % | 48.4 RH % | 74.7 RH % |
|---|---|---|---|
| 0 | r = 0.9872<br>b = 0.17 %/mg implant/h | r = 0.9887<br>b = 0.16 | r = 0.9729<br>b = 0.2 |
| 7 | r = 0.9857<br>b = 0.17 | r = 0.9907<br>b = 0.17 | r = 0.9768<br>b = 0.18 |
| 28 | r = 0.9898<br>b = 0.16 | r = 0.9840<br>b = 0.17 | — |

Other embodiments of the invention will be apparent to those skilled in the art from consideration of the specification and practice of the invention disclosed herein. It is intended that the spesification and examples be considered as exemplary only.

What is claimed is:

1. A delivery device for the controlled release of a biologically active agent or biologically active agents, comprising a dissolvable silica-xerogel particle having a particle size of less than 200 microns and having incorporated within its structure a biologically active agent or agents other than the silica-xerogel itself, wherein the silica-xerogel particle is made by a sol-gel process, wherein gelation of the sol and evaporation of water or solvent occur simultaneously, and wherein the biologically active agent or agents are included in the reaction mixture by the sol-stage of the preparation of the silica-xerogel.

2. The delivery device according to claim 1, wherein the biologically active agent or agents are included in a starting material or starting materials for the preparation of the silica-xerogel.

3. The delivery device according to claim 1, wherein gelation of the sol and evaporation of water or solvent occur by a spray drying method or by a fiber spinning or drawing technique.

4. The delivery device as claimed in claim 1, wherein the silica-xerogel is prepared from tetraethoxysilane as a starting material.

5. The delivery device according to claim 1, wherein the biologically active agent or agents comprise a medicine, a protein, a hormone, a living cell, a bacteria, a virus, or a part thereof.

6. The delivery device according to claim 5, wherein the biologically active agent or agents comprise a medicine.

7. The delivery device according to claim 6, wherein the medicine is toremifene or an acid addition salt thereof.

8. The delivery device according to claim 7, wherein the medicine is toremifene citrate.

9. The delivery device according to claim 1, wherein the delivery device is implantable into a human or animal.

10. The delivery device according to claim 1, wherein the delivery device can be attached mucosally or injected into a human or animal body.

11. A pharmaceutical preparation comprising a delivery device according to claim 1.

12. A method of administering a biologically active agent or biologically active agents to a human or animal, which comprises implanting, injecting or mucosally attaching the delivery device as claimed in claim 1, into the human or animal.

* * * * *